(12) United States Patent
Donnelly et al.

(10) Patent No.: US 10,328,275 B2
(45) Date of Patent: Jun. 25, 2019

(54) MEDICAL DEVICE CONFIGURED TO TEST FOR USER RESPONSIVENESS

(71) Applicant: ZOLL MEDICAL CORPORATION, Chelmsford, MA (US)

(72) Inventors: Edward J. Donnelly, Allison Park, PA (US); John G. Clark, Pittsburgh, PA (US); Steven J. Szymkiewicz, Bethel Park, PA (US); Thomas E. Kaib, Irwin, PA (US); Marshal W. Linder, New Kensington, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/876,322

(22) Filed: Oct. 6, 2015

(65) Prior Publication Data

US 2016/0023014 A1 Jan. 28, 2016

Related U.S. Application Data (63) Continuation of application No. 13/612,400, filed on Sep. 12, 2012, now Pat. No. 9,370,666, which is a
(Continued)

(51) Int. Cl.
*A61N 1/39* (2006.01)
*A61N 1/04* (2006.01)
*A61N 1/372* (2006.01)

(52) U.S. Cl.
CPC .......... *A61N 1/3993* (2013.01); *A61N 1/046* (2013.01); *A61N 1/0484* (2013.01); *A61N 1/39* (2013.01);
(Continued)

(58) Field of Classification Search
CPC .... A61N 1/39; A61N 1/40805; A61N 1/3622; A61N 1/046; A61N 1/3993
See application file for complete search history.

(56) References Cited

U.S. PATENT DOCUMENTS

| 4,094,310 A | 6/1978 | McEachern et al. |
| 4,632,122 A | 12/1986 | Johansson et al. |

(Continued)

FOREIGN PATENT DOCUMENTS

| DE | 2644236 C3 | 4/1981 |
| DE | 102008026871 A1 | 12/2008 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.
(Continued)

*Primary Examiner* — Michael J D Abreu
(74) *Attorney, Agent, or Firm* — ZOLL Medical Corporation (57) ABSTRACT

A medical device is disclosed that includes one or more treatment electrodes, one or more sensors, and one or more controllers connected to the one or more treatment electrodes and one or more sensors. The medical device also includes one or more response mechanisms connected to the one or more controllers. The one or more controllers are configured to receive input from the one or more response mechanism and are also configured to determine whether a patient wearing the medical device actuated the one or more response mechanisms based, at least in part, on the input
(Continued)

received from the one or more response mechanisms. In some disclosed embodiments, the medical device is a wearable defibrillator.

27 Claims, 10 Drawing Sheets

Related U.S. Application Data continuation of application No. 12/150,720, filed on Apr. 30, 2008, now Pat. No. 8,271,082.

(60) Provisional application No. 60/933,550, filed on Jun. 7, 2007.

(52) U.S. Cl.
CPC ......... *A61N 1/3925* (2013.01); *A61N 1/3987* (2013.01); *A61N 1/37217* (2013.01)

(56) References Cited

U.S. PATENT DOCUMENTS

| | | | |
|---|---|---|---|
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,348,008 A | 9/1994 | Bornn et al. |
| 5,365,932 A | 11/1994 | Greenhut |
| 5,472,453 A | 12/1995 | Alt |
| 5,652,570 A | 7/1997 | Lepkofker |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,065,154 A | 5/2000 | Hulings et al. |
| 6,097,982 A | 8/2000 | Glegyak et al. |
| 6,097,987 A | 8/2000 | Milani |
| 6,169,387 B1 | 1/2001 | Kaib |
| 6,169,397 B1 | 1/2001 | Steinbach et al. |
| 6,221,010 B1 | 4/2001 | Lucas |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,405,082 B1 | 6/2002 | Borgenicht |
| 6,406,426 B1 | 6/2002 | Reuss et al. |
| 6,602,191 B2 | 8/2003 | Quy |
| 6,609,023 B1 | 8/2003 | Fischell et al. |
| 6,681,003 B2 | 1/2004 | Linder et al. |
| 6,690,969 B2 | 2/2004 | Bystrom et al. |
| 6,736,759 B1 | 5/2004 | Stubbs et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,893,395 B1 | 5/2005 | Kraus et al. |
| 6,908,437 B2 | 6/2005 | Bardy |
| 6,944,498 B2 | 9/2005 | Owen et al. |
| 6,980,112 B2 | 12/2005 | Nee |
| 6,990,373 B2 | 1/2006 | Jayne et al. |
| 7,074,199 B2 | 7/2006 | Halperin et al. |
| 7,088,233 B2 | 8/2006 | Menard |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,307,509 B2 | 12/2007 | Chriss |
| 7,310,553 B2 | 12/2007 | Freeman |
| 7,340,296 B2 | 3/2008 | Stahmann et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,794,384 B2 | 9/2010 | Sugiura et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,290,574 B2 | 10/2012 | Feild et al. |
| 8,364,221 B2 | 1/2013 | Mannheimer et al. |
| 8,428,704 B2 | 4/2013 | Johnson et al. |
| 9,060,683 B2 | 6/2015 | Tran |
| 9,370,666 B2 | 6/2016 | Donnelly et al. |
| 2003/0004547 A1* | 1/2003 | Owen ................ A61N 1/0452 607/5 |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1* | 9/2003 | Beigel ................ G06K 19/0716 340/10.42 |
| 2003/0195567 A1 | 10/2003 | Jayne et al. |
| 2003/0212311 A1 | 11/2003 | Nova et al. |
| 2004/0204743 A1 | 10/2004 | McGrath et al. |
| 2004/0249419 A1 | 12/2004 | Chapman et al. |
| 2005/0038345 A1 | 2/2005 | Gorgenberg et al. |
| 2005/0049515 A1 | 3/2005 | Misczynski et al. |
| 2005/0131465 A1 | 6/2005 | Freeman et al. |
| 2005/0177051 A1 | 8/2005 | Almen |
| 2005/0246199 A1 | 11/2005 | Futch |
| 2005/0261598 A1 | 11/2005 | Banet et al. |
| 2005/0283198 A1 | 12/2005 | Haubrich et al. |
| 2006/0036292 A1 | 2/2006 | Smith et al. |
| 2006/0079939 A1* | 4/2006 | Chen ................ A61N 1/3956 607/5 |
| 2006/0085049 A1 | 4/2006 | Cory et al. |
| 2006/0136004 A1 | 6/2006 | Cowan et al. |
| 2006/0160522 A1 | 7/2006 | Jennings |
| 2006/0178706 A1 | 8/2006 | Lisogurski et al. |
| 2006/0270952 A1 | 11/2006 | Freeman et al. |
| 2007/0118056 A1 | 5/2007 | Wang et al. |
| 2007/0161913 A1 | 7/2007 | Farrell et al. |
| 2007/0169364 A1 | 7/2007 | Townsend et al. |
| 2007/0239214 A1 | 10/2007 | Cinbis |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0004904 A1 | 1/2008 | Tran |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0103402 A1 | 5/2008 | Stickney et al. |
| 2008/0177341 A1 | 7/2008 | Bowers |
| 2008/0249591 A1 | 10/2008 | Gaw et al. |
| 2008/0287749 A1 | 11/2008 | Reuter |
| 2008/0294019 A1 | 11/2008 | Tran |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0005827 A1 | 1/2009 | Weintraub et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |

(56) References Cited

U.S. PATENT DOCUMENTS

| | | |
|---|---|---|
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0096417 A1 | 4/2009 | Idzik et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2009/0307266 A1 | 12/2009 | Fleizach et al. |
| 2009/0318779 A1 | 12/2009 | Tran |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0102832 A1 | 4/2010 | Bartling et al. |
| 2010/0114243 A1 | 5/2010 | Nowak et al. |
| 2010/0198094 A1 | 8/2010 | Turicchia et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2011/0022105 A9 | 1/2011 | Owen et al. |
| 2011/0054264 A1 | 3/2011 | Fischell et al. |
| 2011/0080294 A1 | 4/2011 | Tanishima et al. |
| 2011/0093840 A1 | 4/2011 | Pynenburg et al. |
| 2011/0098765 A1 | 4/2011 | Patel |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0053479 A1 | 3/2012 | Hopenfeld |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0165684 A1 | 6/2012 | Sholder |
| 2013/0231711 A1 | 9/2013 | Kaib |

FOREIGN PATENT DOCUMENTS

| | | |
|---|---|---|
| EP | 0295497 B1 | 9/1993 |
| EP | 0335356 B1 | 3/1996 |
| EP | 1642616 A2 | 4/2006 |
| EP | 1455640 B1 | 1/2008 |
| EP | 1720446 B1 | 7/2010 |
| JP | 5115450 A | 5/1993 |
| JP | 2002-514107 A | 5/2002 |
| JP | 2003260145 A | 9/2003 |
| JP | 2008513112 A | 5/2008 |
| JP | 2008302225 A | 12/2008 |
| JP | 2008302228 A | 12/2008 |
| JP | 2009510631 A | 3/2009 |
| JP | 2009-521865 A | 6/2009 |
| JP | 2009521260 A | 6/2009 |
| WO | 200002484 A1 | 1/2000 |
| WO | 2004054656 A1 | 7/2004 |
| WO | 2004067083 A2 | 8/2004 |
| WO | 2005082454 A1 | 9/2005 |
| WO | 2006/059190 A2 | 6/2006 |
| WO | 2007019325 A2 | 2/2007 |
| WO | 2007057169 A1 | 5/2007 |
| WO | 2009034506 A1 | 3/2009 |
| WO | 2010025432 A1 | 3/2010 |

OTHER PUBLICATIONS

DeBock, et al., "Captopril treatment of chronic heart failure in the very old," J. Gerontol. (1994) 49: M148-M152.

O'Keeffe et al., "Reproducability and responsiveness of quality of life assessment and six minute walk test in elderly heart failure patients," Heart (1998) 80: 377-382.

Office Action from corresponding German Application No. 102008025709.5 dated Sep. 1, 2017.

* cited by examiner

MEDICAL DEVICE CONFIGURED TO TEST FOR USER RESPONSIVENESS

CROSS-REFERENCE TO RELATED APPLICATIONS

This application is a continuation under 35 U.S.C. § 120 of U.S. application Ser. No. 13/612,400, titled "MEDICAL DEVICE CONFIGURED TO TEST FOR USER RESPONSIVENESS," filed on Sep. 12, 2012, which is a continuation under 35 U.S.C. § 120 of U.S. application Ser. No. 12/150,720, titled "MEDICAL DEVICE CONFIGURED TO TEST FOR USER RESPONSIVENESS," filed on Apr. 30, 2008, now U.S. Pat. No. 8,271,082, each of which is herein incorporated by reference in its entirety. U.S. application Ser. No. 12/150,720 claims priority under 35 U.S.C. § 119(e) to U.S. Provisional Application Ser. No. 60/933,550, filed on Jun. 7, 2007, and incorporates U.S. Provisional Application Ser. No. 60/933,550 by reference in its entirety.

FIELD OF THE INVENTION

This invention relates to devices and methods used to test the responsiveness of a person using or wearing a medical device, such as, for example, a wearable defibrillator.

BACKGROUND OF THE INVENTION

There are many patients susceptible to heart arrhythmias who are at risk of sudden death. For example, patients experiencing a coronary artery occlusion and myocardial infarction are at substantial risk of tachyarrhythmia for several weeks following the coronary artery occlusion. Such patients are generally hospitalized but can be discharged earlier if there is a practical means to protect them from life threatening arrhythmias. One such practical means includes the implantation of an automatic defibrillator. However, patients may also be discharged prior to such an implantation if an external defibrillator, such as, for example, a wearable defibrillator, is available in case they experience a life-threatening tachyarrhythmia.

There are also patients who are placed at an inordinate risk due to the surgery required for implanting an implantable defibrillator. For such patients, implantation would preferably be avoided so such an inordinate risk could be avoided or otherwise mitigated.

Wearable defibrillators are often used to help people with heart conditions that make them susceptible to life threatening cardiac arrhythmias. Such wearable defibrillators are typically configured to quickly treat a life threatening cardiac arrhythmia that is detected while a patient is wearing the device. For example, U.S. Pat. Nos. 4,928,690, 5,078,134, 5,741,306, 5,944,669, 6,065,154, 6,097,987, 6,253,099, 6,280,461 and 6,681,003, disclose wearable defibrillators. The entirety of U.S. Pat. Nos. 4,928,690, 5,078,134, 5,741,306, 5,944,669, 6,065,154, 6,097,987, 6,253,099, 6,280,461 and 6,681,003, are hereby incorporated herein by reference.

Wearable defibrillators are typically used to help patients that either cannot risk an implantation of a defibrillator or are awaiting such an implantation. Occasionally, a patient wearing a wearable defibrillator may appear to be experiencing a life threatening cardiac arrhythmia, but is not having such an event. In such circumstances, the wearable defibrillator is often configured to generate an audible alarm that is designed to stop if a patient provides a required response, such as, for example, pressing one or more response buttons. If a patient fails to press such buttons or otherwise provide a required response, the device may be configured to determine that the patient is unconscious and is undergoing a condition requiring treatment.

Occasionally, a passerby or bystander may interfere with the device by intentionally pressing the response buttons or otherwise providing a response to the wearable device causing the device to withhold treatment to a patient. Such interference can have tragic consequences because it may delay treatment a patient may need. For example, such interference may harm the patient by improperly delaying treatment and, in some cases, may result in patient death.

There is a need for wearable defibrillators and other medical devices to verify that a user providing a response is the patient and not a bystander by preventing anyone except the patient from responding when the patient is undergoing an event that could require treatment. Such verification preferably occurs during episodes of treatable cardiac arrhythmias.

The present invention is directed towards overcoming one or more of the above-mentioned problems.

SUMMARY OF THE INVENTION

A wearable defibrillator is provided that includes one or more controllers, one or more treatment electrodes, one or more sensors and one or more response mechanisms. The one or more controllers are connected to at least one of the one or more sensors and one or more treatment electrodes. The one or more response mechanisms are connected to the one or more controllers and are actuatable by a patient wearing the wearable defibrillator. The one or more controllers are configured to receive input from the one or more response mechanisms and determine whether the patient wearing the wearable defibrillator actuated that one or more response mechanisms based at least in part on the input.

In some embodiments, the one or more response mechanisms can include one or more detectors, one or more transducers, or any combination thereof. In other embodiments, the one or more response mechanisms may include at least one button connected to one or more detectors, one or more transducers or any combination thereof. Preferably, the one or more transducers are biometric transducers and the one or more detectors are biometric sensors. In one embodiment, the one or more transducers of the one or more response mechanisms can be configured to send a marker signal and the one or more detectors of the one or more response mechanisms can be configured to receive the marker signal and transmit at least a portion of the received marker signal to the one or more controllers.

In other embodiments, the wearable defibrillator may also include one or more falloff signal generators connected to at least one of the one or more controllers, one or more sensors and one more treatment electrodes. The one or more falloff signal generators can be configured to transmit a falloff signal through at least a portion of the patient's body. Preferably, the one or more response mechanisms include one or more detectors that are configured to receive the falloff signal when the patient actuates the response mechanism.

In another embodiment, the one or more response mechanisms may include at least one detector configured to detect the capacitance of a person actuating the response mechanism and the one or more controllers are configured to determine a capacitance value from the input. Preferably, the one or more controllers are configured to compare the detected capacitance value to a range of patient capacitance values to determine if the patient actuated the response mechanism.

In some embodiments, the one or more sensors can be configured to receive an ECG signal from the patient and the one or more response mechanisms can include at least one detector configured to receive an ECG signal of a person actuating the one or more response mechanisms. Preferably, the one or more controllers are configured to compare the ECG signal received by the one or more sensors and the ECG signal received by the one or more detectors to determine whether the patient actuated the one or more response mechanisms based at least in part on the input. In one embodiment, the one or more controllers may be configured to compare the ECG signals received by the one or more sensors and one or more detectors by utilizing at least one of morphology comparisons, rate comparisons and R-wave synchronizations.

In other embodiments, the wearable defibrillator can also include at least one accessory item connected to the one or more controllers. Preferably, the one or more accessory items include at least one ring, at least one badge, at least one bracelet or any combination thereof. In one embodiment, the one or more accessory items include at least one identification marker configured to transmit an identification signal. One or more response mechanisms may also include at least one detector configured to receive the identification signal.

A method of testing patient responsiveness of a patient wearing a medical device is also provided. The method includes sensing via sensors on the medical device a condition of the patient requiring treatment, providing a prompt emitted from the medical device that is directed to the patient to elicit a response from the patient upon sensing the condition requiring treatment, and determining if the patient has provided the response if a response is provided.

One embodiment of the method may further include sensing for a signal and, if a response is provided, verifying whether the provided response includes the signal. Preferably, verifying that the response includes the signal occurs during the step of determining whether the patient has provided the response.

Another embodiment of the method can also include measuring capacitance and, if a response is provided, comparing the measured capacitance to a stored patient capacitance to determine whether the patient provided the response. Yet another embodiment of the method may also include detecting an accessory item worn by the patient to determine if the patient has provided the response during the step of determining if the patient has provided the response if a response is provided.

Some embodiments of the method may additionally include sensing ECG signals of the patient and comparing the ECG signals of the patient with ECG signals provided with the response, if a response is provided and is a step used to determine whether the patient provided the response.

Other embodiments of the method can also include requiring entry of at least one of a code and a password. Preferably, requiring entry of a code, password or any combination thereof occurs during the step of determining whether the patient provided the response.

Other details, objects, and advantages of the invention will become apparent as the following description of certain present preferred embodiments thereof and certain present preferred methods of practicing the same proceeds.

BRIEF DESCRIPTION OF THE DRAWINGS

Present preferred embodiments of the invention are shown in the accompanying drawings and certain present preferred methods of practicing the same are also illustrated therein.

DETAILED DESCRIPTION

Figure 1:
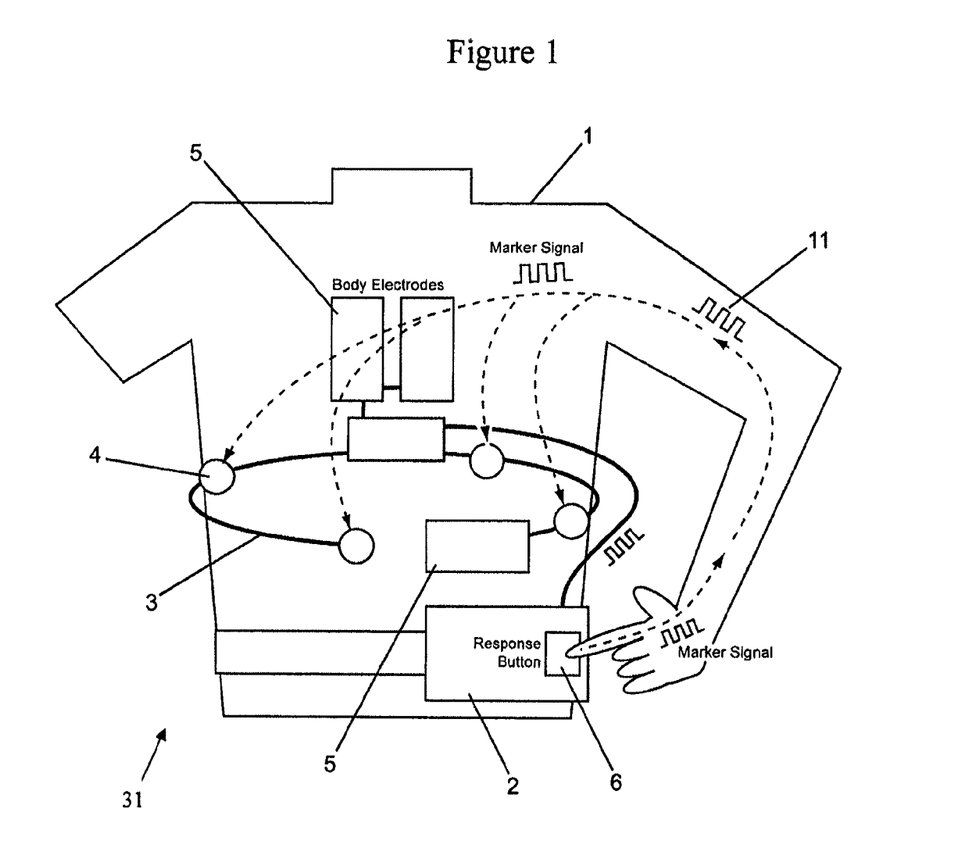
FIG. 1 is a schematic view of a first present preferred embodiment of a wearable defibrillator, which utilizes a marker signal to test for user responsiveness.

A patient 1 wearing a wearable defibrillator 31 that is configured to be worn as a vest is illustrated in FIG. 1. The wearable defibrillator 31 includes sensing electrodes 4 connected to a controller 2 by wiring 3. Treatment electrodes 5 are also connected to the controller 2. The controller 2 includes at least one response button 6. The response button 6 is configured to transmit a unique marker signal 11 into the body of a person touching the button 6. Preferably, the marker signal 11 is transmitted throughout the entire body of the person touching the button 6.

The marker signal 11 may be analog or digital and should have electrical characteristics that are safe for the person touching the response button 6, which preferably will be the patient 1. Preferably, the marker signal 11 is of an electronically generated low amplitude signal that will not harm the patient 1. The marker signal 11 may include encoded information unique to either the patient 1 or the wearable defibrillator 31 worn by the patient 1.

The sensing electrodes 4 are configured to detect the marker signal 11 along with the cardiac ECG 12 or other biometric signals of the patient 1. The controller 2 is configured to receive the marker signal 11 and input from one or more of the sensors 4 that are configured to receive the marker signal 11 and decode the marker signal 11 and input from the one or more sensors 4. The sensors 4 may also be configured to sense ECG signals or other biometric signals.

The controller 2 is configured to verify that the marker signal 11 is being sent into the patient 1. It should be appreciated that the verification of the marker signal 11 can permit the controller 2 to ensure that any person that may actuate the response button 6 cannot prevent the rendering of treatment by the defibrillator unless that person is the patient 1.

Figure 2:
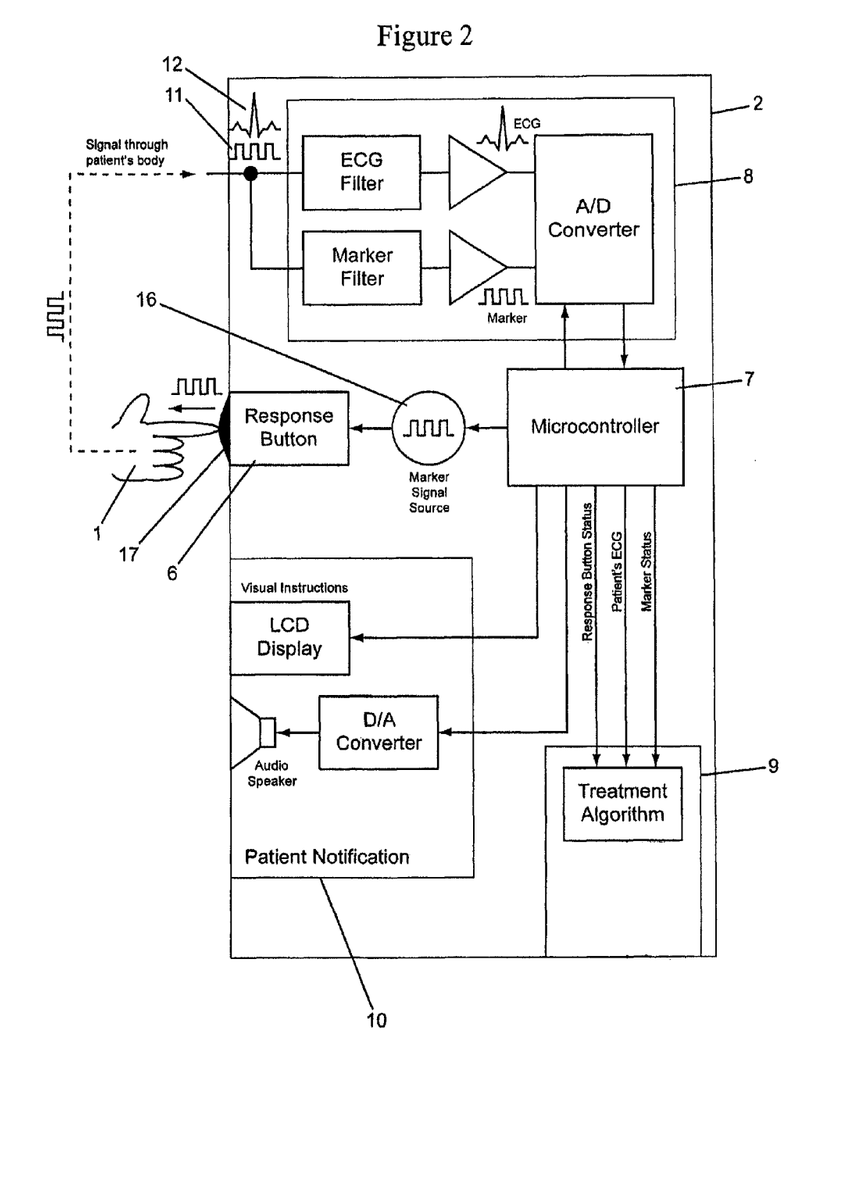
FIG. 2 is a block diagram of a present preferred embodiment of a controller that includes a display and a speaker.

A present preferred embodiment of a circuit that may be used in the controller 2 is illustrated in FIG. 2. The present preferred embodiment of the circuit can be used in the wearable defibrillator embodiment shown in FIG. 1. The circuit includes a marker signal generator 16 that is connected to the response button 6. A microcontroller 7 is connected to the marker signal generator 16, a signal processing circuit 8, a defibrillator processing circuit 9 and a patient notification circuit 10. The response button 6 may include a biometric transducer 17 or other transducer configured to emit the marker signal 11 generated by the marker signal generator 16 into the body of a person touching the button 6.

The signal processing circuit 8 is configured to receive the marker signal 11 transmitted by the transducer 17 into the body of the patient 1. In the event that the maker signal 11 is not received from the body of the patient 1, the microcontroller 7 is configured so that treatment from the treatment electrodes 5 is provided to the patient 1. In the event the signal processing circuit 8 receives the marker signal 11 transmitted by the biometric transducer 17, the microcontroller 7 is configured to process a treatment algorithm or program either stored in the microcontroller 7, operatively connected to the microcontroller 7 or programmed into the defibrillator processing circuit 9.

The treatment algorithm may require the controller 2 to verify that the sensed condition of the patient 1 indicates treatment is needed, that the response button 6 has been activated, and that the marker signal 11 has been received to verify that the person activating the response button 6 is the patient 1. In the event a patient 1 does not activate the response button 6 or other actuator, the defibrillator processing circuit 9 is configured to cause the treatment electrodes 5 to activate to provide treatment to the patient 1. In the event the patient 1 actuates the response button 6, the defibrillator processing circuit 9 or microcontroller 7 is configured so that the treatment electrodes 5 do not provide treatment to the patient 1 since the patient 1 must be conscious in order to actuate the response button 6.

In the event a non-patient presses the response button 6 in response to alarms, instructions or other prompts directed to the patient 1, the controller 2 may be configured to send additional instructions that are relayed to the patient or bystander as audible output, visual output, or both. For example, if a non-patient improperly presses the response button 6, the controller 2 may be configured to ensure instructions are directed to the non-patient that informs the non-patient that treatment will soon be offered to the patient or that the non-patient should not press the response button 6 and that the non-patient should move away from and not touch the patient 1. Of course, the controller 2 may also be configured to cause other instructions or prompts to be transmitted to a non-patient, patient or both.

The microcontroller 7 may also be configured to provide audible instructions, visual instructions, or a combination of both audible and visual instructions to a patient 1 or others located near the patient 1. The microcontroller 7 can be connected to an audio speaker or display located on or in a housing of the controller 2 or located in another device that is worn by the patient 1 or connected to the controller 2. The controller 2 can be configured so that instructions or prompts are directed toward the patient 1. For instance, visual instructions may be displayed on the display, such as for example, an LCD display, or other display connected to the controller 2. The instructions may also be audibly provided to the patient 1 as output transmitted by the speaker or other audible output device.

It should be appreciated that alternate embodiments may include a response button 6 that does not have any mechanical action or functionality. For example, one alternate embodiment may include an actuator affixed to the housing of the controller or an actuator that is integral with the housing of the controller 2. For instance, a portion of the controller housing may include indicia identifying the location of a biometric transducer 17 that is integral with that portion of the controller housing so a patient will know where to place a finger or other portion of the patient's body to respond to alarms or other prompts used to ask the patient to verify that the patient is awake and not in need of treatment.

Figure 3:
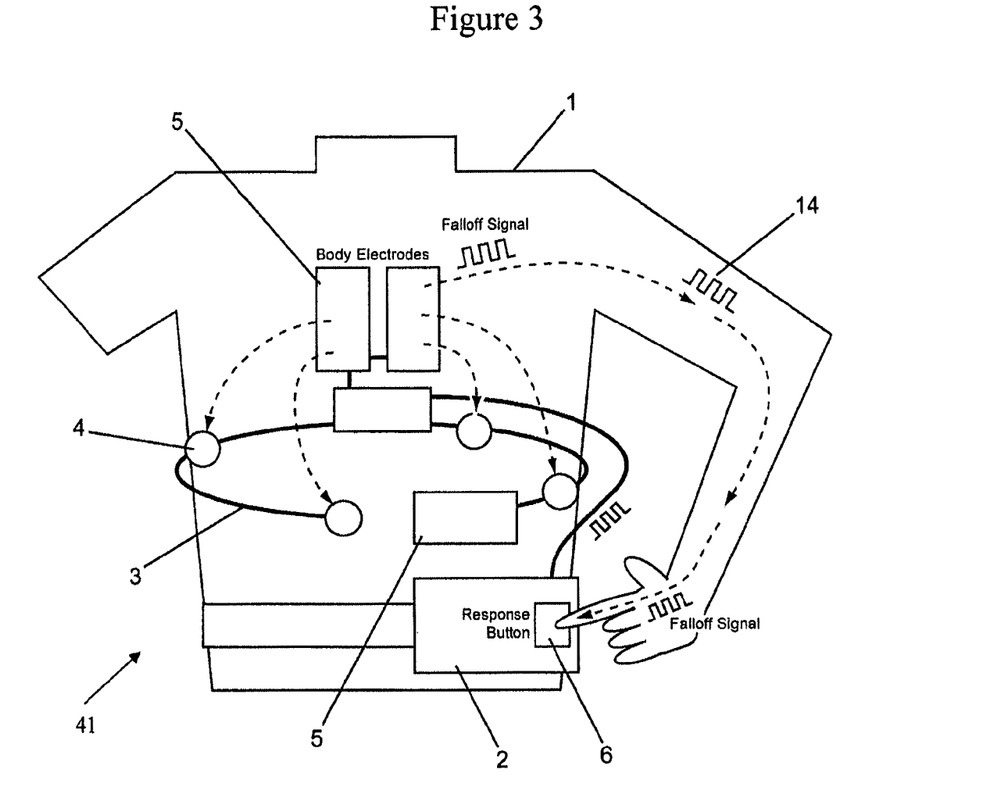
FIG. 3 a schematic view of a second present preferred embodiment of a wearable defibrillator, which utilizes a falloff signal to test for user responsiveness.
Figure 4:
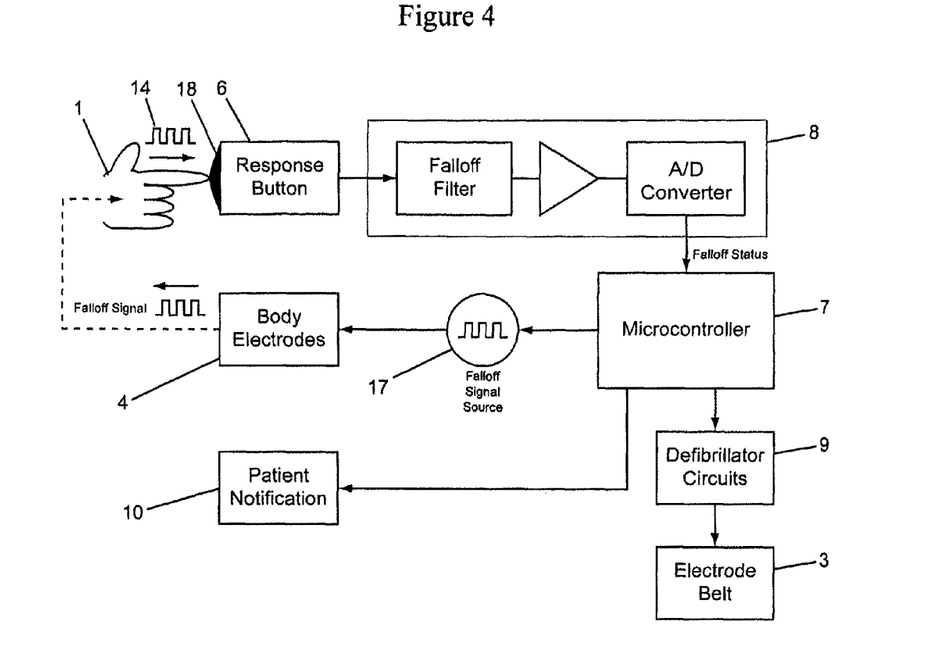
FIG. 4 is a block diagram illustrating a first present preferred method of providing treatment to a patient wearing the second present preferred embodiment of a wearable defibrillator.

A wearable defibrillator can also be configured to utilize a falloff signal 14 to determine that the patient 1 is responding to prompts or instructions and verify that the patient is conscious and not in need of treatment. One embodiment of such a wearable defibrillator is illustrated in FIG. 3, which shows a wearable defibrillator 41 that utilizes a falloff signal 14. A block diagram illustrating the processing of the second present preferred embodiment of the defibrillator 41 is shown in FIG. 4. One or more therapy electrodes 5, or treatment electrodes, are configured to emit a unique falloff marker signal 14 into the body of the patient 1. One or more of the sensors 4 of the defibrillator 41 are configured to sense the falloff signal 14. Preferably, the falloff signal 14 has electrical characteristics that permit the one or more sensors 4 to also sense other biometric signals, such as, for example, ECG signals and other signals. The controller 2 is configured to detect the existence of the falloff signal 14.

The controller 2 may also be configured to detect if a sensor 4 has fallen off the body. For example, the controller 2 may be configured to determine that a sensor 4 has become disconnected from the body of the patient 1 if the falloff marker signal 14 is not detected by one of the sensors 4, but is detected by other sensors 4. If the controller 2 determines such a condition exists, the controller may be configured to provide one or more prompts or instructions to the patient 1 to reattach the dislodged sensor 4. Such a prompt or instruction may be provided on a display connected to the controller 2 or a speaker connected to the controller 2.

The controller 2 includes a microcontroller 7 that is connected to a falloff signal generator 17, the sensors 4, a patient notification circuit 10, defibrillator circuits 9 and a signal processing circuit 8. In some embodiments of the wearable defibrillator, the signal processing circuit 8, patient notification circuit 10 and microcontroller 7 may be located within the housing of the controller 2.

The falloff signal generator 17 is connected to the sensors 4. In other embodiments, the fall off signal generator 17 may be connected to a separate device worn by the patient 1, such as, for example, the treatment electrodes 5.

The response button 6 includes a biometric detector 18 or other biometric sensor that is configured to receive the falloff signal 14 from the body of the person contacting the response button. The signal processing circuit 8 is configured to determine whether the falloff signal 14 has been received from the biometric sensor 18.

The controller 2 is configured to determine whether the response button 6 has been activated and, if so, whether the falloff signal 14 was received from the biometric sensor 18. If both the falloff signal 14 was received and the response button 6 was actuated, the controller 2 is configured to determine that the patient 1 actuated the response button 6. It should be appreciated that such a determination can be used to verify that a patient 1 is responding to prompts or instructions displayed or played by notification devices such as, for example, a monitor or speaker, connected to the controller 2.

Figure 5:
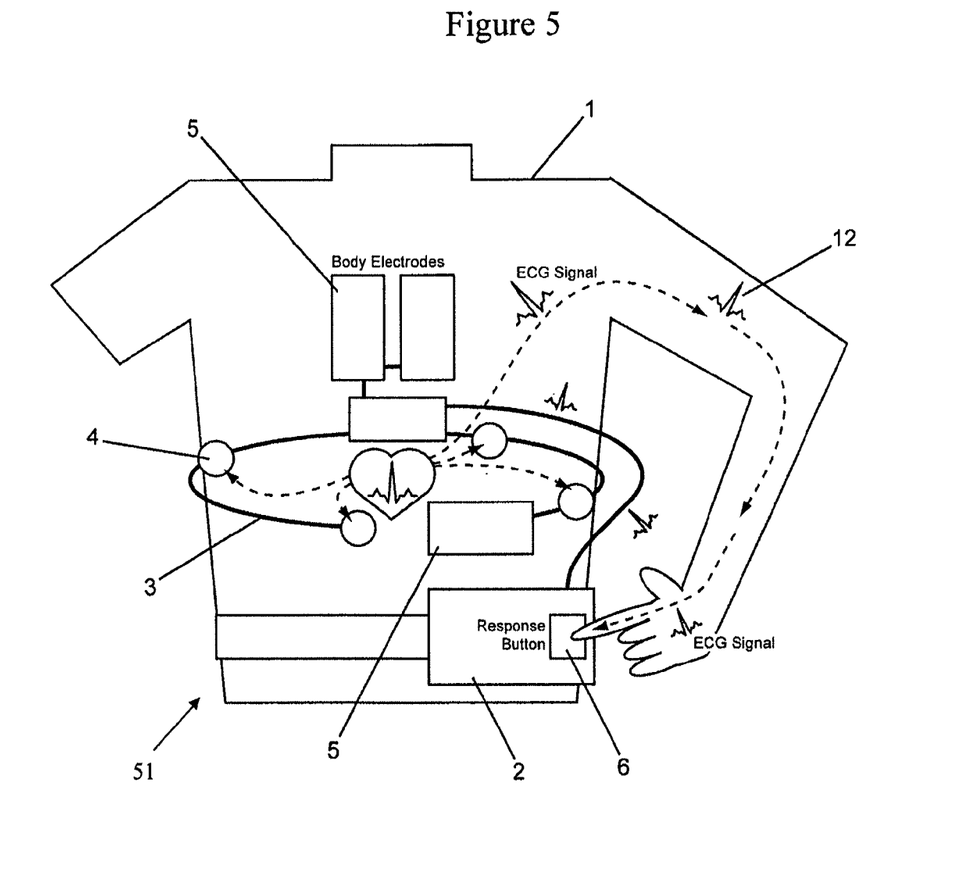
FIG. 5 is a schematic view of a third present preferred embodiment of a wearable defibrillator, which utilizes ECG signals to test for user responsiveness.
Figure 6:
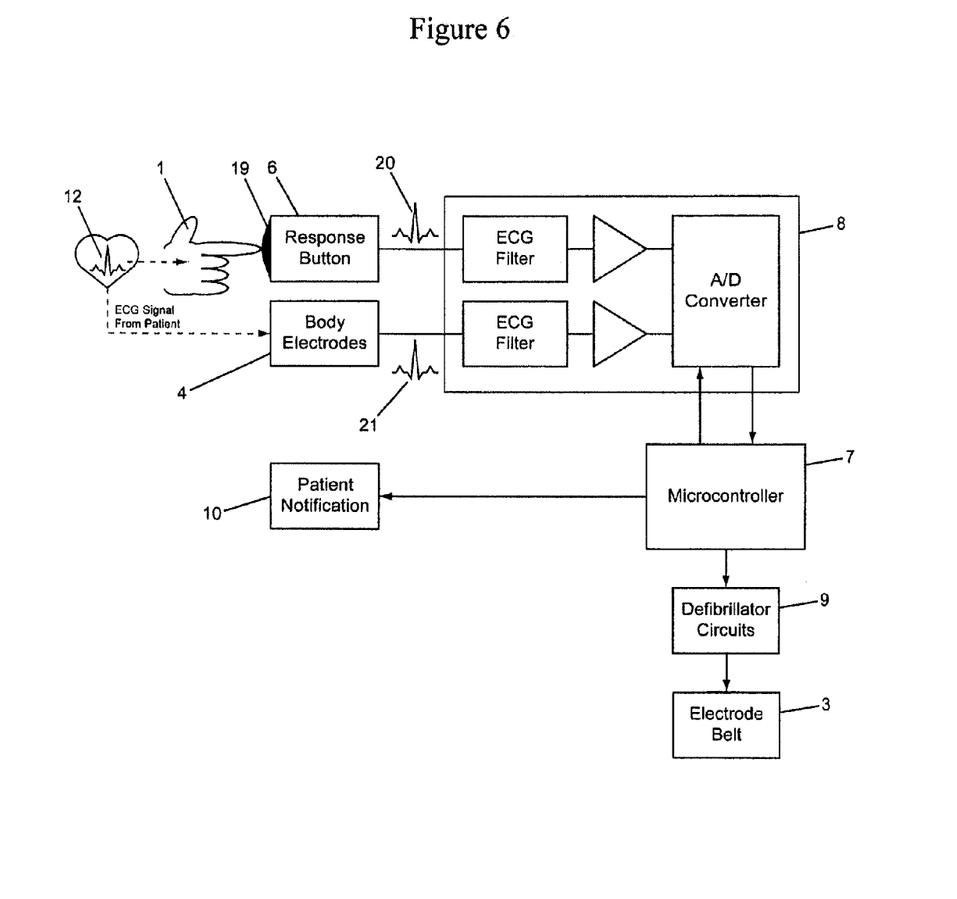
FIG. 6 is a block diagram illustrating a second present preferred method of providing treatment to a patient wearing the third present preferred embodiment of a wearable defibrillator.
Figure 7:
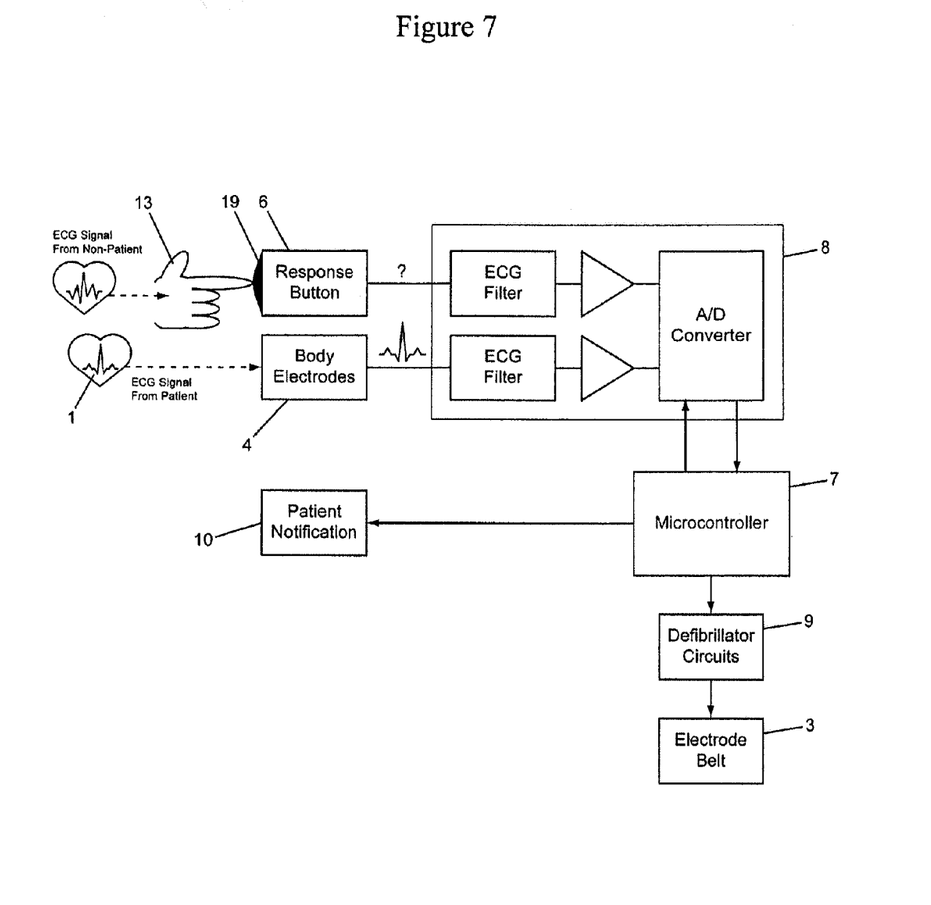
FIG. 7 is a block diagram illustrating the second present preferred method of providing treatment to a patient wearing the third present preferred embodiment of a wearable defibrillator when a non-patient provides a response to a prompt emitted from the third present preferred embodiment of a wearable defibrillator.

A third embodiment of a wearable defibrillator 51 is illustrated in FIGS. 5, 6 and 7. The response button 6 of the wearable defibrillator 51 includes an ECG detector 19 that is configured to sense the ECG signal 12 of the patient 1 wearing the defibrillator. The ECG detector 19 may be attached to response button 6 such that at least a portion of the detector 19 extends out of the outer surface of the response button 6, may be attached on the outer surface of the response button 6, or may be otherwise connected to the response button 6. Preferably, the ECG detector 19 is an ECG electrode that is similar in design to ECG sensors 4 that are attached to the defibrillator 51.

The controller 2 of the defibrillator 51 may be configured to confirm that the patient 1 is actuating the response button 6 by correlating any ECG signal 20 received by the ECG detector 19 with the ECG signals 20, 21 received by the ECG sensors 4 worn by the patient 1. The controller 2 can be configured to compare the ECG signals received by the ECG detector 19 to the ECG signals received by the ECG sensors 4 worn by the patient 1 in various ways. For example, the controller 2 may be configured to utilize morphology comparisons, rate comparison, R-wave synchronization or any combination thereof to compare the ECG signals 20, 21 and determine whether the ECG signals 20, 21 received by ECG detector 19 to verify that the person actuating the response button 6 is the patient 1.

It should be appreciated that if a person that is not the patient actuates the response button 6, a correlating ECG signal should not be detected by the controller 2. As illustrated in FIG. 7, in the event a non patient actuates the response button 6, the ECG signal received by the ECG detector 19 will be an ECG signal that is not a match to the patient ECG signal being received by the sensors 4. It should also be appreciated that if a person that is not the patient 1 does not have a common ground reference to the circuitry of the defibrillator 51, a corrupt signal or no signal at all may be received by the controller 2. The signal processing circuit 8 or microcontroller 7 can be configured to recognize that the signal received from the ECG detector 19 does not match the signals received from the sensors 4. The controller 2 may be configured to disregard any actuation of the response button 6 that the controller 2 determines was made by a person that is not the patient 1. The controller 2 may also be configured to provide prompts or instructions to a non-patient that has actuated a response button to inform the non-patient that he or she should not respond to the prompts, request additional input to verify the person actuating the response button is not the patient 1, or inform the non-patient that treatment is about to be provided to the patient 1 and, consequently, that he or she should move away from the patient 1.

Figure 8:
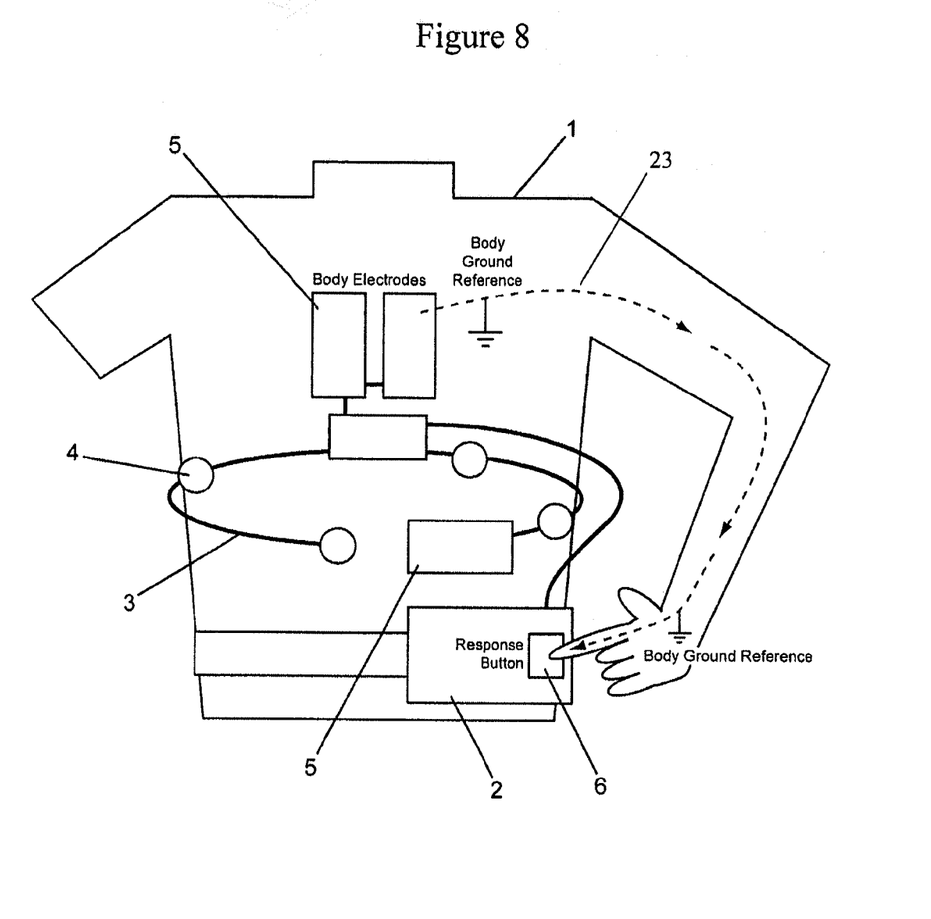
FIG. 8 is a schematic view of a fourth present preferred embodiment of a wearable defibrillator, which utilizes a touch sensor to test for user responsiveness.
Figure 9:
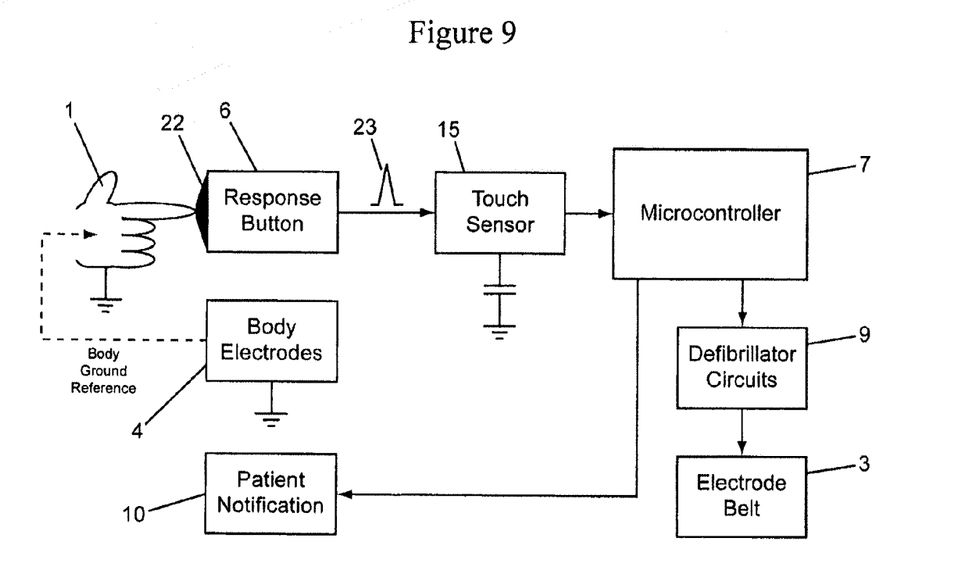
FIG. 9 is a block diagram illustrating a third present preferred method of providing treatment to a patient wearing the fourth present preferred embodiment of a wearable defibrillator.

Another embodiment of a wearable defibrillator, illustrated in FIGS. 8 and 9, depict a wearable defibrillator 61 configured to verify a patient 1 is actuating a response button 6 or actuating some other response mechanism by detecting a capacitance value of the person or object actuating the response button. The capacitance value can be used to verify whether the patient 1 or some other person has actuated the response mechanism. For example, the measured capacitance value can be compared with a value or range of values related to the patient that are stored in the controller to verify that the patient actuated the response mechanism. The stored capacitance value or range of capacitance values may be stored in the controller 2 during the start-up procedure for the defibrillator or may be stored and saved by the controller 2 during an initial use of the defibrillator by the patient 1 and reused by the controller 2 until a new value or range of values is saved to the controller 2 to replace the old value or range of values.

The controller 2 of wearable defibrillator 61 includes a response button 6 that has a capacitive detector 22 or other capacitive sensor. Preferably, the capacitive detector 22 is a capacitive type electrode. The capacitive detector 22 is connected to a touch sensor 15 or other circuitry that is configured to detect variations in capacitance 23 due to patient specific physical interaction with the response button 6 and capacitive detector 22. As illustrated in FIG. 9, the controller 2 can be configured to determine when the response button 6 has been actuated by the patient 1 by comparing the capacitance value sensed by the capacitance detector 22 with a capacitance value or range of capacitance values stored in the controller 2 or in memory connected to the controller 2. If the capacitance value is not within the stored range of values or is not the stored value, the controller 2 is configured to determine that the patient 1 did not actuate the response button 6. The controller 2 may be configured to disregard actuation of the response button 6 if it is determined that the patient 1 did not actuate the response button 6 and may also be configured to provide one or more prompts or instructions to the non-patient that may have actuated the response button 6.

Accessory items may also be used to verify that a patient is providing input to a wearable defibrillator. For example, the embodiment of the wearable defibrillator 71 shown in FIG. 10 includes one or more accessory items that transmit an identification marker 26 to the controller 2 of the defibrillator. The accessory items may be a finger ring 24, bracelet 25, necklace, lanyard, earring, badge, name tag, any other accessory that may be worn by a user or any combination thereof.

Figure 10:
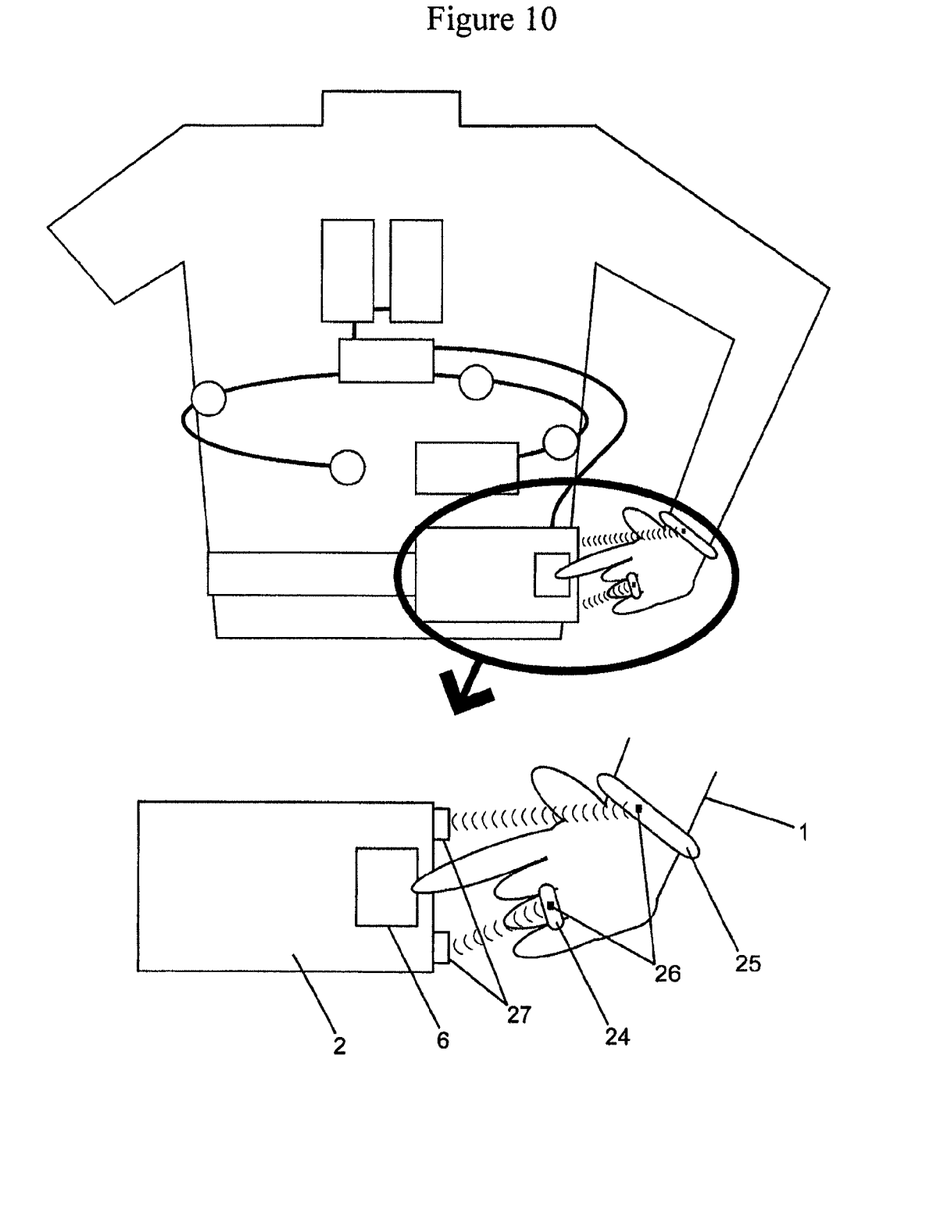
FIG. 10 is a schematic view of a fifth present preferred embodiment of a wearable defibrillator, which utilizes one or more accessory items that transmit an identification marker to a monitoring device to verify user responsiveness.

The controller 2 can include one or more receivers or other detectors that are configured to receive the identification marker transmitted by the one or more accessory items. The controller 2 may also be configured to determine when an accessory item is close to the housing of the controller 2 or a monitor or other display connected to the controller 2. For example, a magnetic proximity detector 27 or other proximity sensor configured to detect one or more of the accessory items may be provided on or connected to the controller 2.

The controller 2 can be configured to utilize the presence of the accessory item to verify that the patient is actuating a response mechanism such as for example response button 6. The controller 2 may also be configured to verify that all response mechanism actuations are made by a patient during a treatment sequence run or controlled by the controller 2. For example, the controller 2 can be configured to ignore the actuation of a response mechanism or transmit additional patient prompts, alarms or instructions through a display or speaker connected to the controller 2 if a correlating identification accessory is not sensed or is not sensed to be within a certain distance from the controller 2 or receiver.

The location of the response mechanism, such as, for example, one or more response buttons 6 may be sized and configured to avoid accidental activation or a response by someone other than the patient. For instance, the response mechanism may include one or more buttons that are located on the housing of the controller 2 in a hidden or obscured location. One example of such a hidden location may be a recessed portion of the controller housing. Another example of such a hidden location may be locating one or more response buttons 6 under a latch or cover that is moveably connected to the housing of the controller 2 or a display connected to the controller 2. As yet another example, the response mechanism may be a device that has one or more actuators that are wirelessly connected to the controller 2. Such a device may be within the pocket of an article of clothing worn by a patient or positioned in another location a typical passerby would be unlikely to see or find.

It should be appreciated that multiple response buttons 6, response switches or other response mechanism may be connected to the controller 2. Preferably, two or more response buttons are used such that simultaneous activation of the two or more buttons is required to actuate the response mechanism. Such a configuration can reduce false positive detection.

Of course, actuation of a response mechanism may also include actuating one or more response buttons in a particular sequence. For instance, the controller 2 or response mechanism may be configured so that actuation of a response mechanism occurs when a patient presses different buttons in a particular sequence or moves one or more response switches or other buttons to different positions. For example, if an embodiment included a response mechanism that had a switch, the response mechanism could be configured so that movement of the switch from a first position to a second position and then back to the first position within a certain time interval was necessary to actuate the response mechanism.

It should be understood that one or more additional sensors may be used to avoid accidental activation or a response by a non-patient. Such additional sensors may include a biometric sensor such as for example a fingerprint, voice, or face recognition sensor. The controller 2 can be configured to require input from the additional sensor that correlates with patient data stored in the controller 2 or stored in memory connected to the controller 2 to verify that a patient is actuating a response mechanism or otherwise providing input to the controller 2.

Of course, the controller 2 can also be configured to use other verification methods to provide additional input that confirms a patient is providing input to the controller 2. For example, a feedback loop that includes a current path to the controller 2 or a current path to a display device connected to the controller 2 may also be used to verify that a patient is providing input to the controller 2.

One or more additional sensors may also include a motion, position or oximetry detector located on another area of the patient's body and connected to the controller 2. The controller 2 could be configured to obtain input from such sensors to aid the controller 2 in determining the condition of the patient 1.

Embodiments of a wearable defibrillator may also include a controller 2 configured to receive a code or password from a patient 1. The password or code may be provided to the controller 2 by use of one or more buttons, a key pad, or other data entry device connected to or located on the controller 2. The controller 2 could be configured to require entry of the password or code at any time during the sequence of alarms or other prompts or instructions to prevent someone other than the patient from inadvertently giving a response when the patient 1 is unconscious. Of course, such a code could also include pressing one or more response buttons, one or more response switches, or other response actuators in a certain sequence.

Of course, since the controller 2 can also be configured to verify that the response mechanism is working properly to avoid or mitigate errors resulting from broken or damaged response mechanisms. In one embodiment, the controller 2 can be configured to routinely test the response mechanism for proper functionality or monitor the response mechanism to predict a failure of the response mechanism. For instance, the controller 2 can be configured to conduct a response test each time the defibrillator is turned on. In the event the controller 2 does not receive input from the response mechanism or otherwise recognize any actuation of the response mechanism during a test of the response mechanism, the controller 2 may be configured to provide one or more audible or visual prompts to the patient 1 that informs the patient 1 the response mechanism is broken or needs to be repaired. The controller 2 may also be configured to use an alternate responsiveness test method if one is available or inform the patient 1 that to prevent treatment, it would be necessary to remove the power source from the controller 2. The controller 2 may also be configured so that it deactivates the defibrillator after it determines that the response mechanism is not functioning properly.

In the event the controller 2 is configured to monitor response mechanism operations to predict the failure of the response mechanism, the controller 2 may be configured to process a prediction algorithm configured to predict future failure of the response mechanism. When a failure is predicted, the controller 2 can be configured to alert the patient 1, disable the defibrillator, or both.

It should be appreciated that variations of the present preferred embodiments discussed above may be made. For example, embodiments of the wearable defibrillator can be sized and configured to be worn as a harness, belt, vest, or other wearable device. As another example, a response mechanism can include one or more response buttons, response switches, other response actuators or any combination thereof. As yet another example, the controller 2 of the wearable defibrillator may be connected to different components of the wearable defibrillator by one or more direct or indirect wireless connections, direct or indirect wired connections, or any combination thereof. As yet another example, the treatment electrodes may include various types of treatment electrodes known to those skilled in the art, such as, for example, pulse electrodes disclosed in U.S. Pat. No. 5,078,134.

While certain present preferred embodiments of the wearable defibrillator and certain embodiments of methods of practicing the same have been shown and described, it is to be distinctly understood that the invention is not limited thereto but may be otherwise variously embodied and practiced within the scope of the following claims.

What is claimed is:

1. A wearable defibrillator comprising:
   at least one sensing electrode configured to sense an electrocardiogram signal of a patient wearing the wearable defibrillator;
   at least one treatment electrode configured to provide treatment to the patient wearing the wearable defibrillator;

at least one response mechanism configured to be actuated by the patient; and at least one controller operatively connected to the at least one sensing electrode and the at least one treatment electrode and wirelessly connected to the at least one response mechanism, the at least one controller being configured to receive the electrocardiogram signal of the patient, determine, based on at least the electrocardiogram signal of the patient, whether the patient is experiencing a cardiac arrhythmia, provide at least one prompt to elicit a response from the patient in response to determining that the patient is experiencing the cardiac arrhythmia, provide treatment to the patient via the at least one treatment electrode in response to determining that the patient is experiencing the cardiac arrhythmia and the at least one response mechanism has not been actuated, and withhold treatment to the patient via the at least one treatment electrode in response to the patient actuating the at least one response mechanism.

2. The wearable defibrillator of claim 1, wherein the wearable defibrillator is configured to be worn as at least one of a harness, belt, and vest.

3. The wearable defibrillator of claim 2, wherein the at least one response mechanism is configured to be disposed within a pocket of an article of clothing worn by the patient.

4. The wearable defibrillator of claim 3, wherein the at least one response mechanism includes at least one button.

5. The wearable defibrillator of claim 4, wherein the at least one button is sized and configured to avoid accidental activation by the patient.

6. The wearable defibrillator of claim 1, further comprising at least one of a display and a speaker operatively connected to the at least one controller.

7. The wearable defibrillator of claim 6, wherein the at least one prompt is at least one of an audible prompt and a visual prompt.

8. The wearable defibrillator of claim 6, wherein the at least one of the display and the speaker is located on or in a housing of the at least one controller.

9. The wearable defibrillator of claim 6, wherein the at least one of the display and the speaker is located in a device that is separate from the at least one controller.

10. The wearable defibrillator of claim 1, wherein the at least one sensing electrode is wirelessly connected to the at least one controller.

11. The wearable defibrillator of claim 10, wherein the at least one treatment electrode is wirelessly connected to the at least one controller.

12. The wearable defibrillator of claim 1, wherein the at least one prompt is a first prompt, and wherein the at least one controller is further configured to provide at least one additional prompt directed to at least one of the patient and a bystander in response to determining that the patient is experiencing the cardiac arrhythmia and the at least one response mechanism has not been actuated.

13. The wearable defibrillator of claim 12, wherein the at least one additional prompt indicates that treatment will soon be provided to the patient wearing the wearable defibrillator via the at least one treatment electrode.

14. The wearable defibrillator of claim 1, wherein the at least one response mechanism is configured to be disposed within a pocket of an article of clothing worn by the patient.

15. The wearable defibrillator of claim 1, wherein the at least one response mechanism includes a touch sensor.

16. The wearable defibrillator of claim 1, wherein the at least one prompt is at least one of an audible prompt and a visual prompt.

17. The wearable defibrillator of claim 1, further comprising at least one additional sensor operatively connected to the at least one controller, the at least one additional sensor including at least one of a motion detector, a position detector, and an oximetry detector.

18. The wearable defibrillator of claim 1, wherein the at least one response mechanism includes at least one button.

19. The wearable defibrillator of claim 18, wherein the at least one button is sized and configured to avoid accidental activation by the patient.

20. The wearable defibrillator of claim 19, wherein the at least one sensing electrode is wirelessly connected to the at least one controller.

21. The wearable defibrillator of claim 20, wherein the at least one treatment electrode is wirelessly connected to the at least one controller.

22. A wearable defibrillator system, comprising:

at least one of a harness, vest, and belt configured to be worn by a patient;

at least one sensing electrode configured to sense an electrocardiogram signal of the patient;

at least one treatment electrode disposed in the at least one of the harness, vest, and belt, the at least one treatment electrode configured to provide treatment to the patient;

at least one controller operatively connected to the at least one sensing electrode and the at least one treatment electrode, the at least one controller being configured to receive the electrocardiogram signal of the patient, to determine, based on at least the electrocardiogram signal of the patient, whether the patient is experiencing a cardiac arrhythmia, and to provide at least one prompt to elicit a response from the patient in response to determining that the patient is experiencing the cardiac arrhythmia; and a response device configured to wirelessly communicate with the at least one controller to cause the at least one controller to withhold treatment to the patient via the at least one treatment electrode in response to input from the patient.

23. The wearable defibrillator system of claim 22, further comprising at least one of a display and a speaker operatively connected to the at least one controller, and wherein the at least one prompt is at least one of an audible prompt and a visual prompt.

24. The wearable defibrillator system of claim 22, wherein the response device includes at least one button configured to receive the input from the patient, and the at least one button is sized and configured to avoid accidental activation by the patient.

25. The wearable defibrillator system of claim 22, wherein the at least one sensing electrode is wirelessly connected to the at least one controller.

26. A method of testing responsiveness of a patient wearing a defibrillator comprising:

sensing an electrocardiogram signal of the patient wearing the defibrillator;

determining whether the patient is experiencing a cardiac arrhythmia based on at least the electrocardiogram signal of the patient;

providing at least one prompt to elicit a response from the patient in response to determining that the patient is experiencing the cardiac arrhythmia;

providing treatment to the patient via at least one treatment electrode in response to determining that the patient is experiencing the cardiac arrhythmia and that no response is provided; and wirelessly communicating the response to at least one controller of the defibrillator to cause the defibrillator to withhold treatment to the patient via the at least one treatment electrode in response to the patient providing the response.

27. The method of claim 26, wherein providing the at least one prompt includes providing at least one of an audible prompt and a visual prompt.

* * * * *